(12) United States Patent
Chanduszko et al.

(10) Patent No.: US 8,518,099 B2
(45) Date of Patent: Aug. 27, 2013

(54) LOW FRICTION VASCULAR IMPLANT DELIVERY DEVICE

(75) Inventors: Andrzej J. Chanduszko, Chandler, AZ (US); Enrique Abarca, Chandler, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 653 days.

(21) Appl. No.: 11/869,938

(22) Filed: Oct. 10, 2007

(65) Prior Publication Data

US 2009/0099636 A1   Apr. 16, 2009

(51) Int. Cl.
*A61F 2/06* (2006.01)
(52) U.S. Cl.
USPC .......................................... 623/1.11; 606/194
(58) Field of Classification Search
USPC ............. 623/1.11, 1.13, 1.38, 1.54; 606/108, 606/200, 191, 198, 192
See application file for complete search history.

(56) References Cited

U.S. PATENT DOCUMENTS

| | | | |
|---|---|---|---|
| 5,755,722 A | 5/1998 | Barry et al. | |
| 6,056,759 A | 5/2000 | Fiedler | |
| 7,163,553 B2 | 1/2007 | Limon | |
| 2002/0058951 A1 | 5/2002 | Fiedler | |
| 2003/0144670 A1* | 7/2003 | Pavcnik et al. | 606/108 |
| 2006/0009835 A1* | 1/2006 | Osborne et al. | 623/1.13 |
| 2006/0009839 A1* | 1/2006 | Tan | 623/1.38 |
| 2006/0015133 A1* | 1/2006 | Grayzel et al. | 606/192 |
| 2006/0161135 A1 | 7/2006 | VanDerWoude | |
| 2009/0312832 A1 | 12/2009 | Delap | |

OTHER PUBLICATIONS

Aug. 25, 2009 International Search Report in international application PCT/US2008/079604.
Aug. 25, 2009 Written Opinion of the International Searching Authority in international application PCT/US2008/079604.
Apr. 22, 2010 International Preliminary Report on Patentability in international application PCT/US2008/079604.

* cited by examiner

*Primary Examiner* — Tuan V Nguyen
*Assistant Examiner* — Tin Nguyen
(74) *Attorney, Agent, or Firm* — Rutan & Tucker, LLP

(57) ABSTRACT

A vascular implant delivery device is disclosed and can include a body and a syringe attachment formed in the body. Further, the device can include an outer sheath extending from the body. The outer sheath can include a distal end that can be configured to receive a vascular implant. The device can also include at least three implant support structures that can extend radially inward from the distal end of the outer sheath. The implant support structures can be configured to support and guide a vascular implant moving through the outer sheath. Additionally, the device can include an inner carrier catheter slidably disposed within the outer sheath.

24 Claims, 14 Drawing Sheets

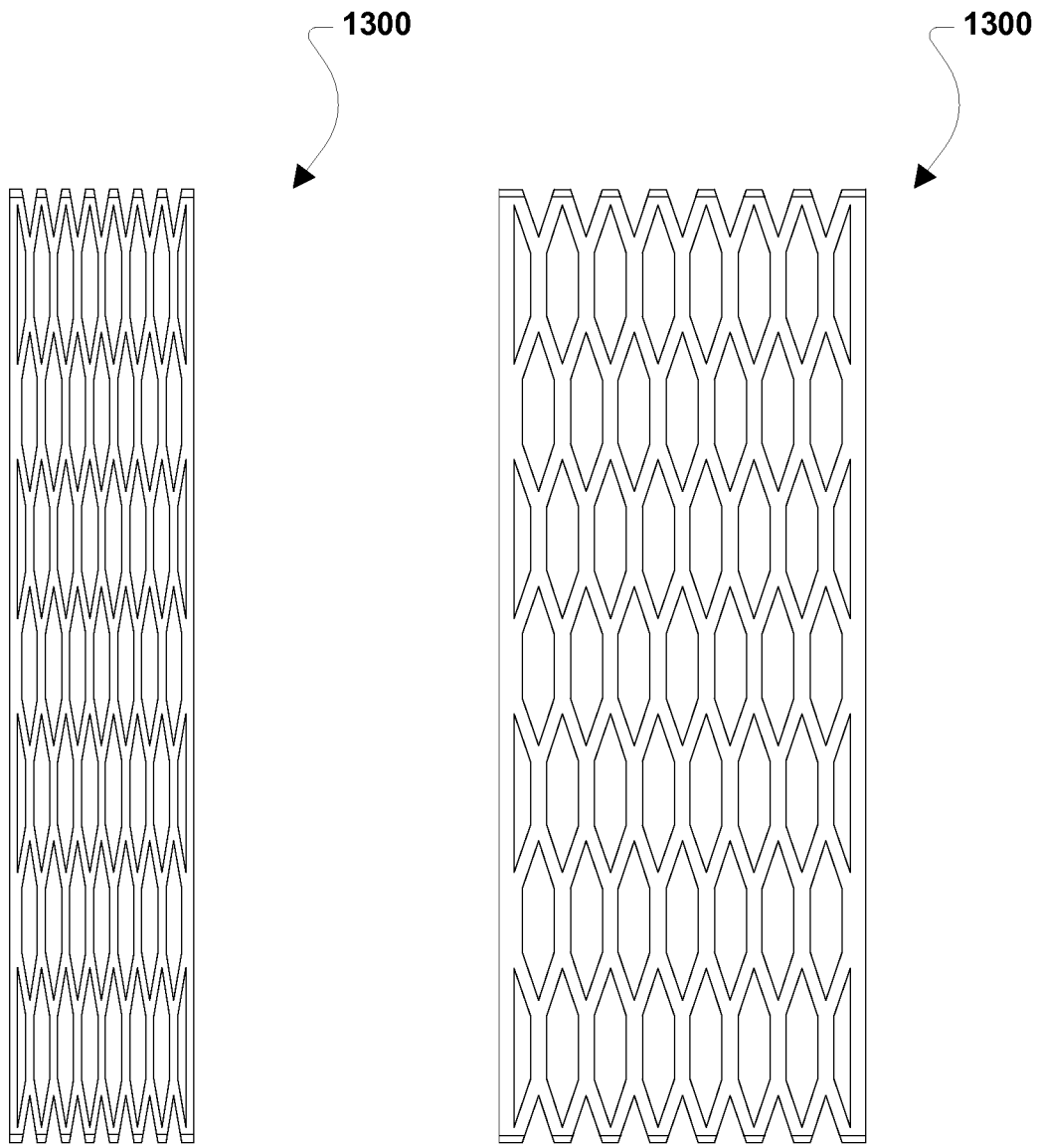
FIG. 13  FIG. 14

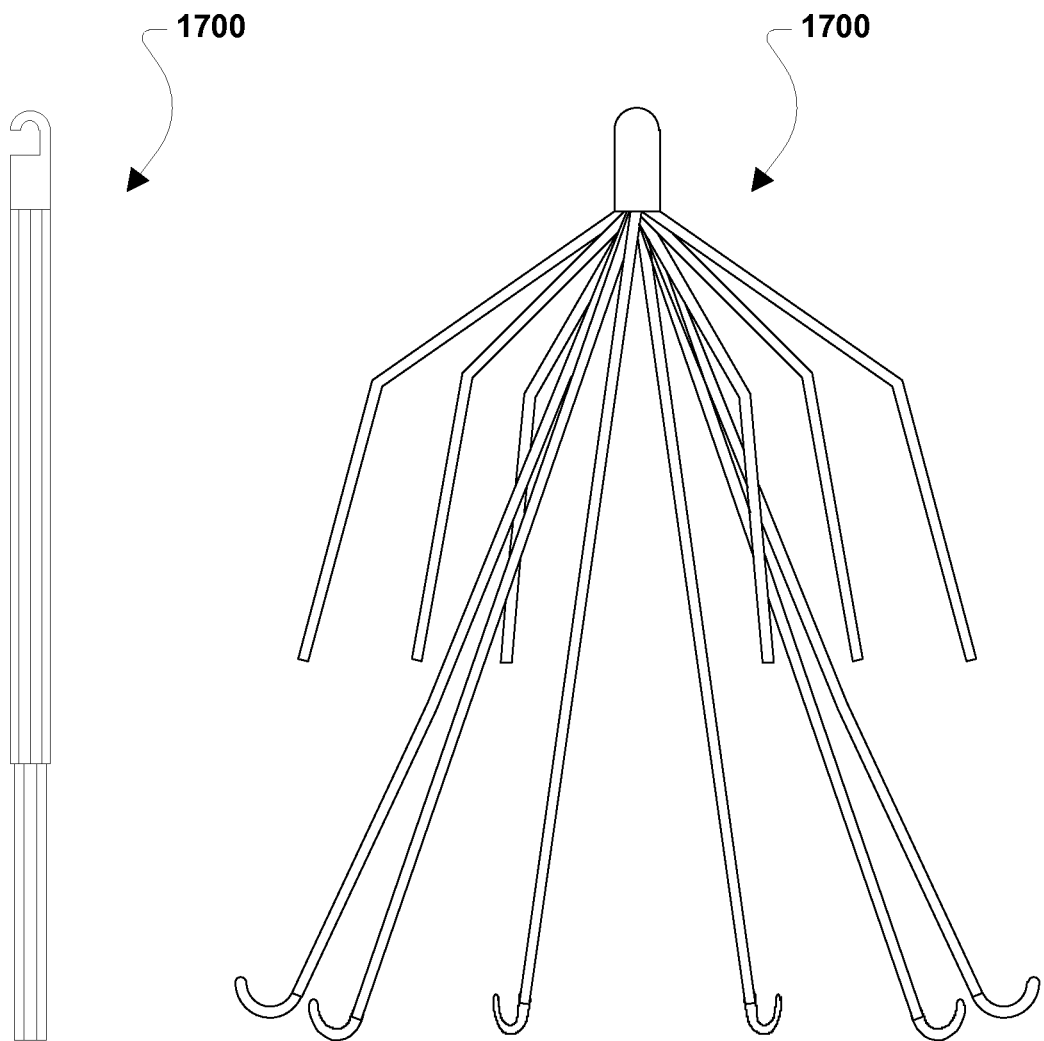
FIG. 17     FIG. 18

LOW FRICTION VASCULAR IMPLANT DELIVERY DEVICE

FIELD OF THE DISCLOSURE

The present disclosure relates generally to surgical devices. More specifically, the present disclosure relates to vascular implant delivery devices.

BACKGROUND

Vascular implants can include stents, stent grafts, intravenous filters, etc. Other vascular treatment devices can include angioplasty balloons, etc. Oftentimes, these implants and devices can be delivered to a location within a patient using a catheter. Typically, the catheter is moved into a predetermined location within the cardiovascular system of a patient. Then, the implant or device can be moved through the catheter and expelled, or otherwise expressed, from the catheter to the targeted location.

While state of the art delivery devices are effective to deliver vascular implants, further improvements in delivery devices and implant/delivery structures continue to be demanded in the industry.

BRIEF DESCRIPTION OF THE DRAWINGS

FIG. 13 is a plan view of a stent in a collapsed configuration;

FIG. 14 is a plan view of the stent in an expanded configuration;

FIG. 17 is a plan view of an intravenous filter in a collapsed configuration;

FIG. 18 is a plan view of the filter in an expanded configuration; and

DETAILED DESCRIPTION OF THE DRAWINGS

A vascular implant delivery device is disclosed and can include a body and a syringe attachment formed in the body. Further, the device can include an outer sheath extending from the body. The outer sheath can include a distal end that can be configured to receive a vascular implant. The device can also include at least three implant support structures that can extend radially inward from the distal end of the outer sheath. The implant support structures can be configured to support and guide a vascular implant moving through the outer sheath. Additionally, the device can include an inner carrier catheter slidably disposed within the outer sheath.

In another embodiment, a vascular implant delivery device is disclosed and can include an outer sheath having an outer surface, an inner surface, and a lumen bound by the inner surface. Further, the device can include at least three longitudinal fibers partially embedded within the outer sheath. Each longitudinal fiber at least partially extends radially into the lumen of the outer sheath.

In yet another embodiment, an implant delivery assembly is disclosed and can include a body and a syringe attachment formed in the body. The assembly can also include an outer sheath extending from the body. The outer sheath can include a distal end configured to receive a vascular implant. Moreover, the assembly can include at least three implant support structures that can extend radially inward from the distal end of the outer sheath. The implant support structures can be configured to support and guide a vascular implant moving through the outer sheath. The assembly can also include an inner carrier catheter slidably disposed within the outer sheath and a vascular implant disposed within the distal end of the outer sheath.

In still another embodiment, a method of making an outer sheath is disclosed and can include installing a plurality of fibers in a mandrel having an outer periphery. The fibers can extend along a length of the mandrel and extend radially outward beyond the outer periphery of the mandrel. The method can also include forming a material around the mandrel in a generally tubular shape to form an outer sheath. The material of the outer sheath can partially encompass each of the plurality of fibers.

In another embodiment, a method of delivering a vascular implant to a patient is disclosed and can include moving an outer sheath to a target area wherein the vascular implant is located within the outer sheath, commencing delivery of a lubricant through the outer sheath wherein the lubricant flows at least partially around the vascular implant, and expelling the vascular implant from the outer sheath.

Description of a Vascular Implant Delivery Device

Figure 1:
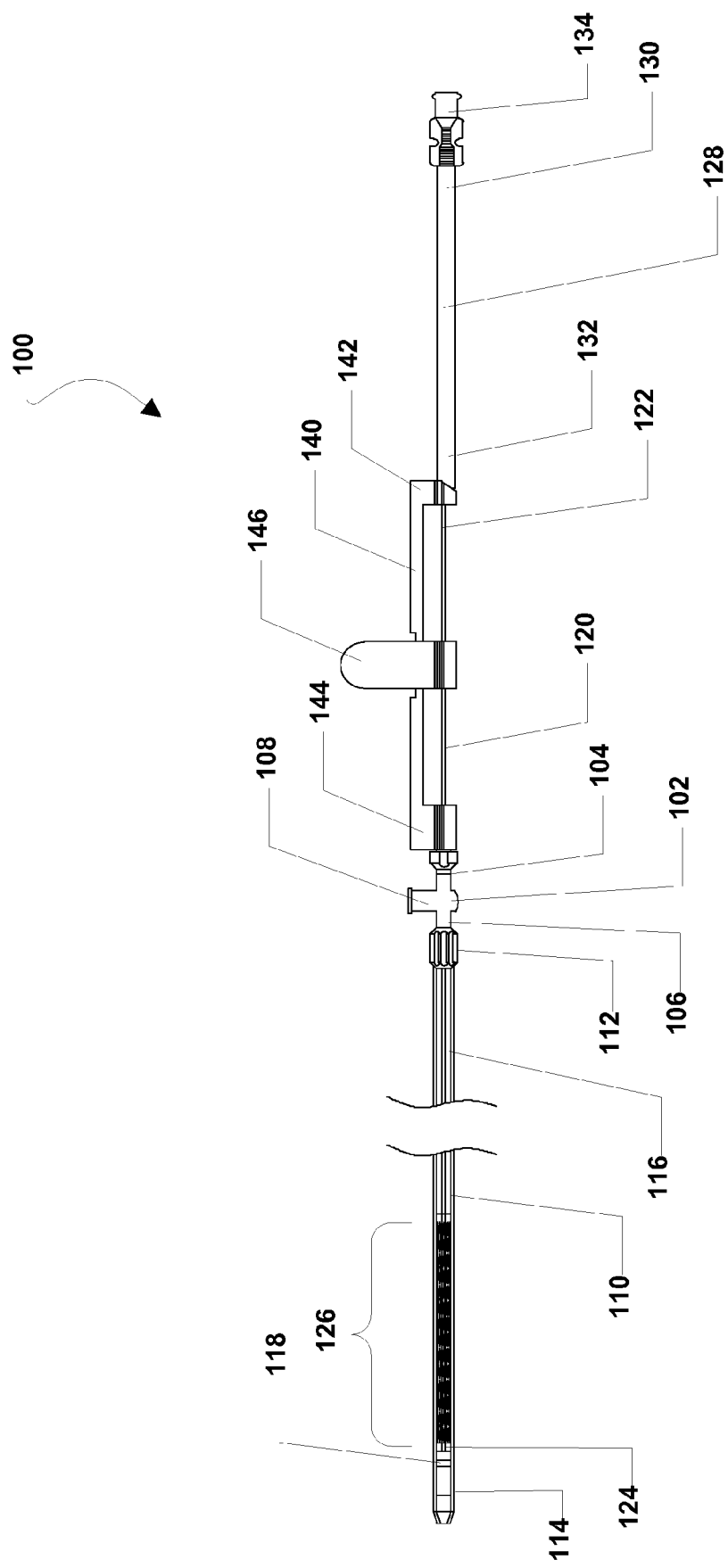
FIG. 1 is a plan view of a vascular implant delivery device.

Referring to FIG. 1, a stent delivery device is shown and is generally designated 100. As shown, the stent delivery device 100 includes a body 102 having a proximal end 104 and a distal end 106. A first syringe attachment 108 can be formed in the body 102 between the proximal end 104 and the distal end 106. In a particular embodiment, the first syringe attachment 108 can be a Luer syringe attachment. The first syringe attachment 108 can provide fluid communication to a lumen formed within an outer sheath 110, described below.

FIG. 1 indicates that the stent delivery device 100 can include an outer sheath 110. The outer sheath 110 can include a proximal end 112 and a distal end 114. Further, the outer sheath 110 can extend from the distal end 106 of the body 102 of the stent delivery device 100. In particular, the proximal end 112 of the outer sheath 110 can be attached to the distal end 106 of the body 102 of the stent delivery device 100. The distal end 114 of the outer sheath 110 can be relatively soft and rounded. The outer sheath 110 can include a lumen 116 formed therein. Further, the distal end 114 of the outer sheath 110 can include a radiopaque band 118.

As illustrated in FIG. 1, the stent delivery device 100 can further include an inner carrier catheter 120 slidably disposed within the outer sheath 110. The inner carrier catheter 120 can extend through the body 102 of the stent delivery device 100 and into the lumen 116 formed in the outer sheath 110. The inner carrier catheter 120 can be coaxial with the outer sheath 110. Further, the inner carrier catheter 120 can include a proximal end 122 and a distal end 124. The inner carrier catheter 120 can be formed with a lumen (not shown) that can be sized to fit over a guide wire. In particular, the lumen of the inner carrier catheter 120 can fit over a 0.035 inch guide wire.

As shown in FIG. 1, a stent 126 can be compressed between the inner catheter 120, e.g., the distal end of the inner catheter 120, and the outer sheath 110. A handle 128 can be attached to, or otherwise extend from, the proximal end 122 of the inner carrier catheter 120. The handle 128 can include a proximal end 130 and a distal end 132. The proximal end 130 of the handle 128 can include a second syringe attachment 134. In a particular embodiment, the second syringe attachment 134 can be a Luer syringe attachment. The second syringe attachment 134 can provide fluid communication with the lumen formed within the inner carrier catheter 120.

The stent delivery device 100 can also include a safety clip 140 installed between the body 102 of the stent delivery device 100 and the handle 128 of the inner carrier catheter 120. The safety clip 140 can include a proximal end 142 and a distal end 144. Further, the safety clip 140 can include a butterfly handle 146 between the proximal end 142 of the safety clip 140 and the distal end 144 of the safety clip 140. In a particular embodiment, the safety clip 140 can be installed between the body 102 of the stent delivery device 100 and the handle 128 of the inner carrier catheter 120 such that the proximal end 142 of the safety clip 140 abuts the distal end 132 of the handle 128 and the distal end 144 of the safety clip 140 abuts the proximal end 104 of the body 102.

The safety clip 140 can fit over the inner carrier catheter 120. Further, the safety clip 140 can prevent the body 102 of the stent delivery device 100 from moving relative to the handle 128 of the inner carrier catheter 120. Further, the safety clip 140 can prevent the outer sheath 110 from sliding relative to the inner carrier catheter 120. During use, the stent delivery device 100 can be threaded into a cardiovascular system of a patient to a target area. The radio opaque band 118 formed on the outer sheath 110 can be used to guide the stent delivery device into the cardiovascular system of a patient, e.g., with the aid of fluoroscopy. Further, a pair of radiopaque bands on the stent 126 can aid in positioning the stent 126 within the patient. Once the stent 126 is properly positioned, the butterfly handle 146 can be squeezed in order to remove the safety clip 140 from the inner carrier catheter 120 and the stent delivery device 100. Thereafter, the body 102 of the stent delivery device 100 can be moved toward the handle of the inner carrier catheter 120 in order to slide the outer sheath 110 off of the stent 126 and expose the stent 126 inside the patient.

Once the stent 126 is exposed within the patient, body temperature will allow the stent 126 to move to a shape memory configuration, e.g., an expanded configuration, within the patient, and be deployed within the patient. After the stent 126 is deployed, the inner carrier catheter 120 can be withdrawn from the patient.

Figure 2:
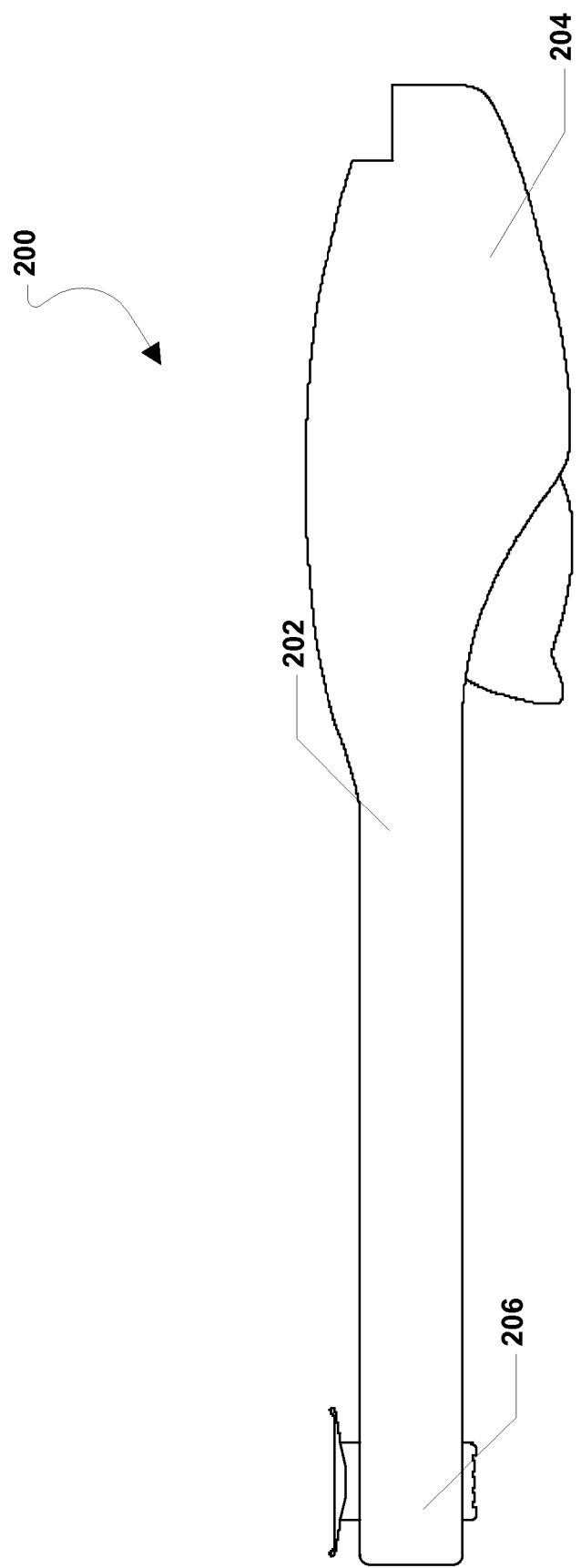
FIG. 2 is a plan view of a handle for a vascular implant delivery device.
Figure 3:
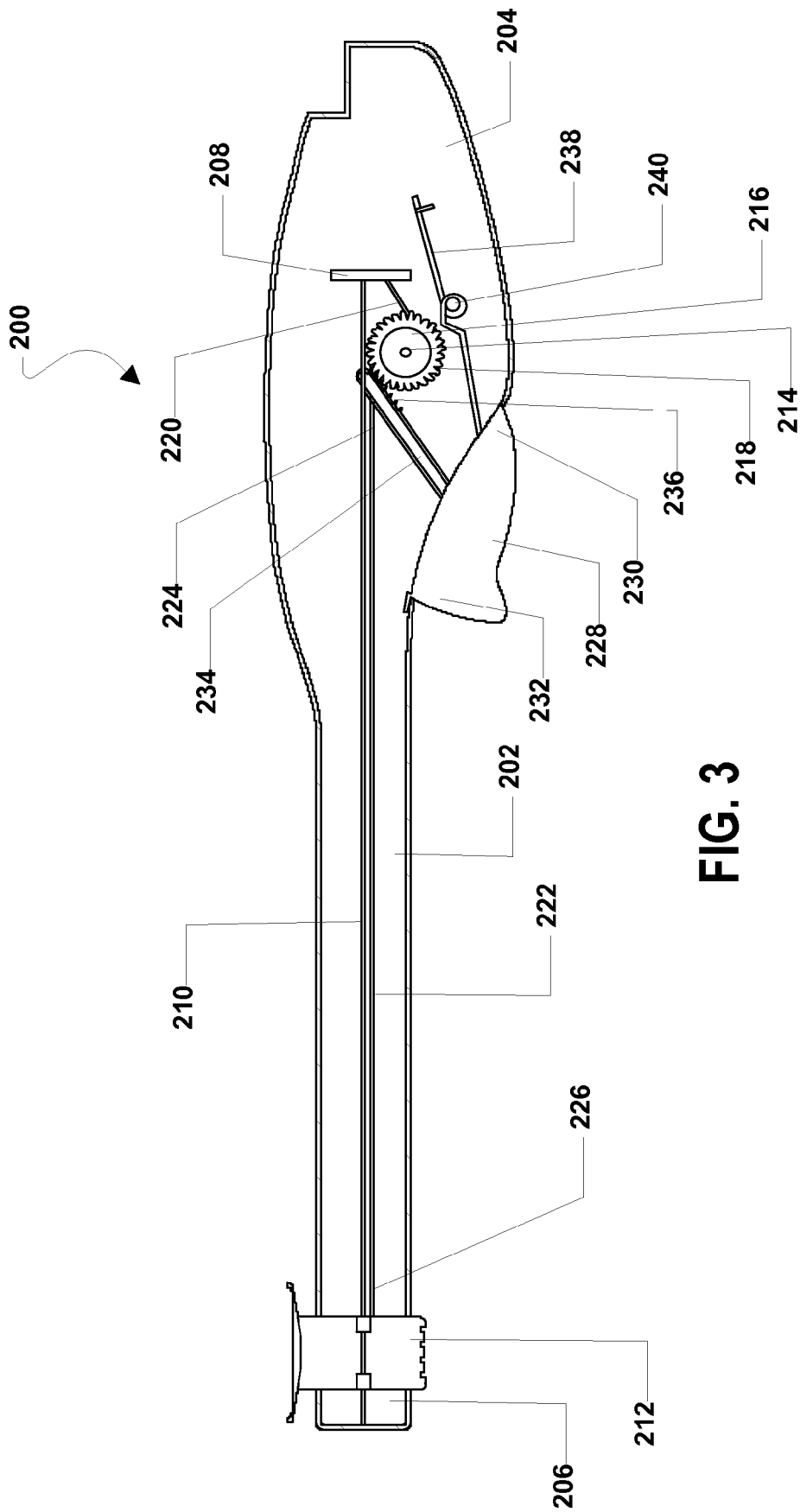
FIG. 3 is a cross-section view of the handle.

FIG. 2 and FIG. 3 illustrate a handle assembly, generally designated 200 that can be used in conjunction with the stent delivery system 100, described above. As shown in FIG. 2 and FIG. 3, the handle assembly 200 can include a housing 202. The housing 202 can be hollow and can include a proximal end 204 and a distal end 206.

As depicted in FIG. 3, a rail support structure 208 can be disposed within the housing 202 near the proximal end 204 of the housing 202. A pair of rails 210 can extend between the distal end 206 of the housing 202 and the rail support structure 208. The handle assembly 200 can also include a carrier 212 that can be slidably disposed on the rails 210. In a particular embodiment, the carrier 212 can be configured to receive the body of a stent delivery system, e.g., the stent delivery system 100, described above.

A shaft 214 can extend from the housing 202 near the rail support structure 208, e.g., between the rail support structure 208 and the distal end 206 of the housing 202. In a particular embodiment, the shaft 214 is substantially perpendicular to the rails 210. A ratchet wheel 216 can be rotatably disposed on the shaft 214. The ratchet wheel 216 can be formed with a plurality of teeth 218 around the outer periphery of the ratchet wheel 216. The handle assembly 200 can also include a pawl 220 extending from the rail support structure 208. The pawl 220 can be configured to engage the ratchet wheel 216, e.g., the teeth 218 of the ratchet wheel 216, and permit rotation of the ratchet wheel 216 in a single direction, e.g., clockwise.

FIG. 3 further shows that the handle assembly 200 can include a cable 222. The cable 222 can include a proximal end 224 and a distal end 226. The cable 222 can extend within the housing along the length of the rails 210. Further, the proximal end 224 of the cable 222 can be wrapped, or otherwise disposed, around the ratchet wheel 216. The distal end 226 of the cable 222 can be attached, or otherwise affixed, to the carrier 212. As the ratchet wheel 216 is rotated, the cable 222 can be rolled onto the ratchet wheel 216 and the carrier 212 can slide along the rails 210 toward the proximal end 204 of the housing 202.

As illustrated in FIG. 3, the handle assembly 200 can also include a trigger 228 extending from the housing 202. The trigger 228 can include a proximal end 230 and a distal end 232. The proximal end 230 of the trigger 228 can be rotatably engaged with the housing 202 and the distal end 232 of the trigger 228 can be free. As such, the trigger 228 can rotate around the proximal end 230 of the trigger 228.

FIG. 3 further indicates that an arm 234 can extend from the trigger 228. The arm 234 can include a plurality of teeth 236 that can engage the teeth 218 formed on the ratchet wheel 216. The handle assembly 200 can also include a spring 238 installed around a post 240 within the housing 202. The spring 238 can bias the trigger 228 outward relative to the housing 202. In a particular embodiment, when the trigger 228 is squeezed inward relative to the housing 202, the arm 234 can rotate the ratchet wheel 216 and cause the carrier 212 to slide within the housing 202 toward the proximal end 204 of the housing 202.

Figure 4:
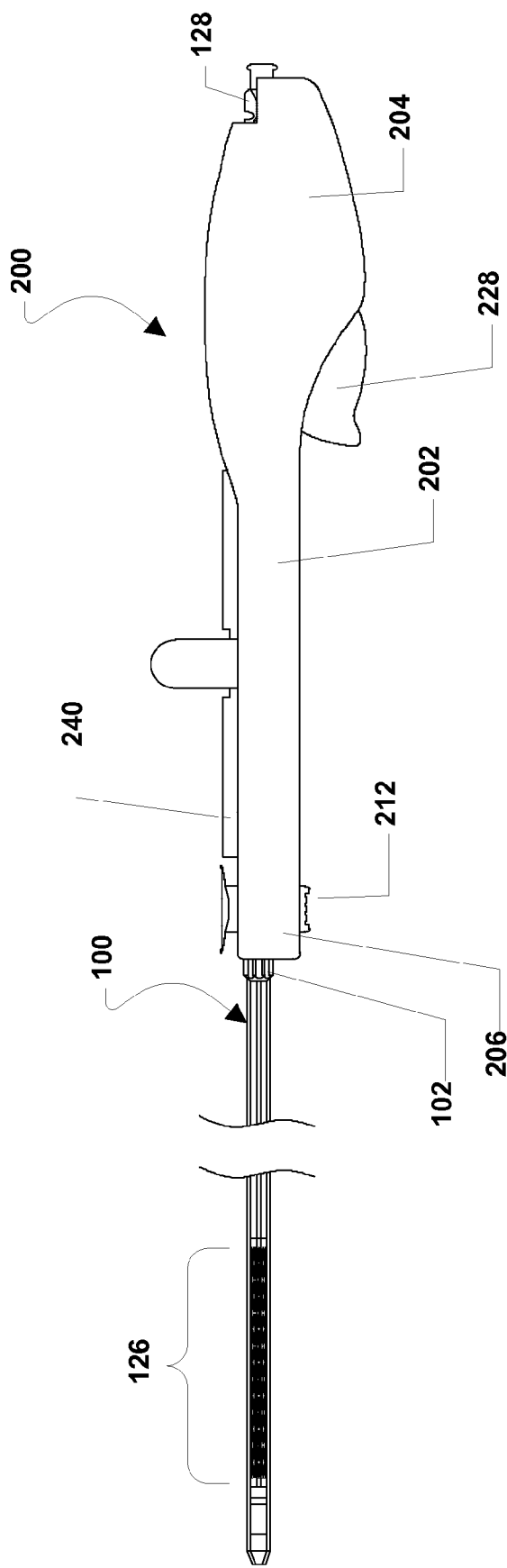
FIG. 4 is a plan view of the vascular implant delivery device engaged with the handle.

In a particular embodiment, the stent delivery device 100 can be engaged with the handle assembly 200 as shown in FIG. 4. Specifically, the body 102 of the stent delivery device 100 can be inserted within the carrier 212. Further, the inner carrier catheter 120 can be installed within the housing 202 of the handle assembly 200 so that the handle 128 of the inner carrier catheter 120 extends through the proximal end 204 of the housing 202. The handle 128 of the inner carrier catheter 120 can be engaged with the housing 202 so that the handle 128 does not move relative to the housing during operation of the handle assembly 200.

Accordingly, the safety clip 140 can be removed from the stent delivery device 100 and the trigger 228 can be squeezed to move the carrier 212 within the handle assembly 200 toward the proximal end 204 of the housing 202. As the carrier 212 moves, the body 102 of the stent delivery device 100 can be moved toward the handle 128 of the inner carrier catheter 120. As the body 102 of the stent delivery device 100 moves toward the handle of the inner carrier catheter 120, the outer sheath 110 can slide off of the stent 126 and expose the stent 126 inside a patient.

Description of a Sheath

Figure 5:
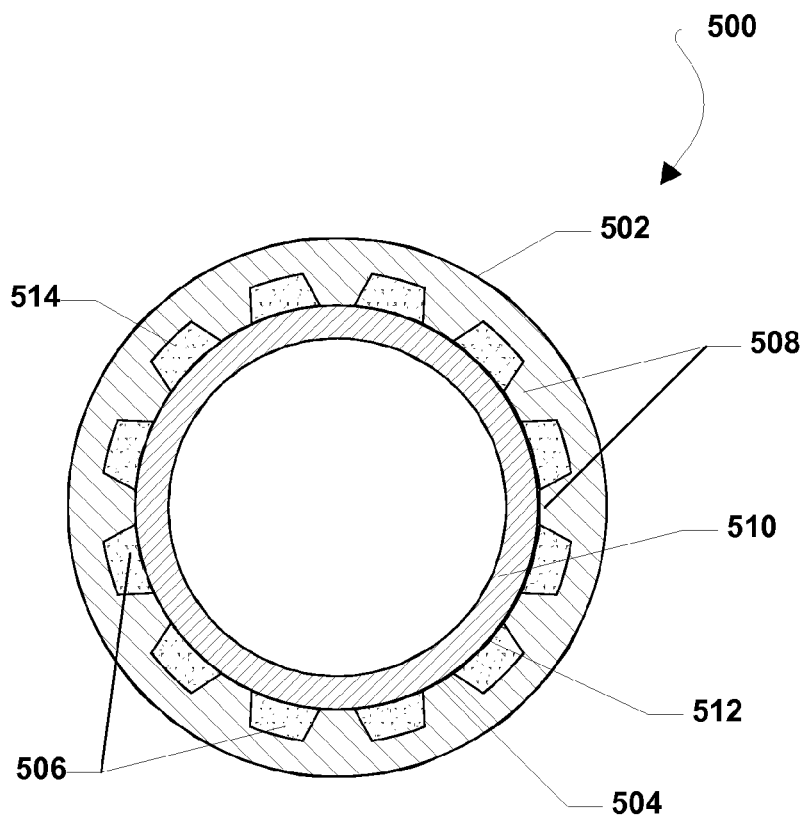
FIG. 5 is a cross-section view of a first embodiment of a sheath for vascular implant delivery device.

Referring now to FIG. 5, a sheath is shown and is generally designated 500. The sheath 500 is shown in cross-section. Further, the sheath 500 can be used as an outer sheath in conjunction with a vascular implant delivery device, e.g., the vascular implant delivery device 100 shown in FIG. 1 through FIG. 4.

As illustrated, the sheath 500 can include an outer surface 502 and an inner surface 504. A plurality of internal longitudinal voids 506 can be formed in sheath 500. Specifically, the internal longitudinal voids 506 can extend into the inner surface 504 of the sheath 500. In a particular embodiment, the internal longitudinal voids 506 can be equally spaced around the inner surface 504 of the sheath 500.

As indicated in FIG. 5, the sheath 500 can also include a plurality of implant support structures 508. In particular, each implant support structure 508 can be formed between adjacent longitudinal voids 506 formed in the sheath 500. As such, the implant support structures 508 can be equally spaced around the inner surface 504 of the sheath 500. The support structures 508 can be shaped as shown. However, the support structures 508 can be shaped otherwise, e.g., circular, rectangular, triangular, irregular, etc.

In a particular embodiment, a vascular implant 510 can be slidably disposed within the sheath 500. The vascular implant 510 can be a stent, a stent graft, an intravenous filter, or some other implant that is delivered to a patient using a cannulated delivery device. Alternatively, the vascular implant 510 can be an angioplasty balloon that is temporarily deployed and inflated to treat a patient. FIG. 5 indicates that the vascular implant 510 can include an outer surface 512.

As shown in FIG. 5, the implant support structures 508 can contact the outer surface 512 of the vascular implant 510. Moreover, each longitudinal void 506 can act as a longitudinal channel and a lubricant 514 can be introduced into the sheath 500 around the vascular implant 510. In a particular embodiment, the lubricant can be saline solution. FIG. 5 indicates that each longitudinal void 506 can be at least partially filled with the lubricant and the lubricant can surround the vascular implant 510. The lubricant can reduce friction between the implant support structures 508 and the vascular implant 510. As such, the force require to expel the vascular implant 510 from the sheath is substantially reduced.

Figure 6:
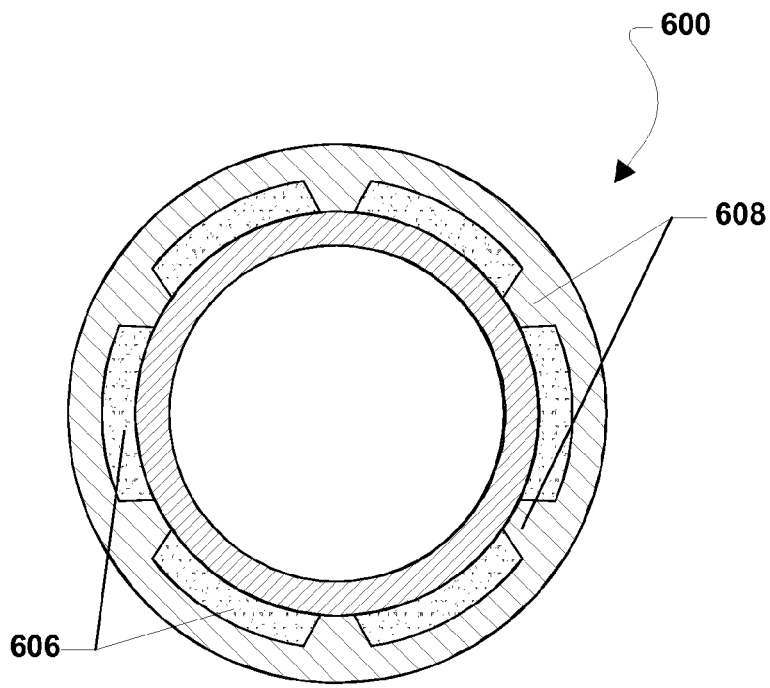
FIG. 6 is a cross-section view of a second embodiment of a sheath for a vascular implant delivery device.
Figure 7:
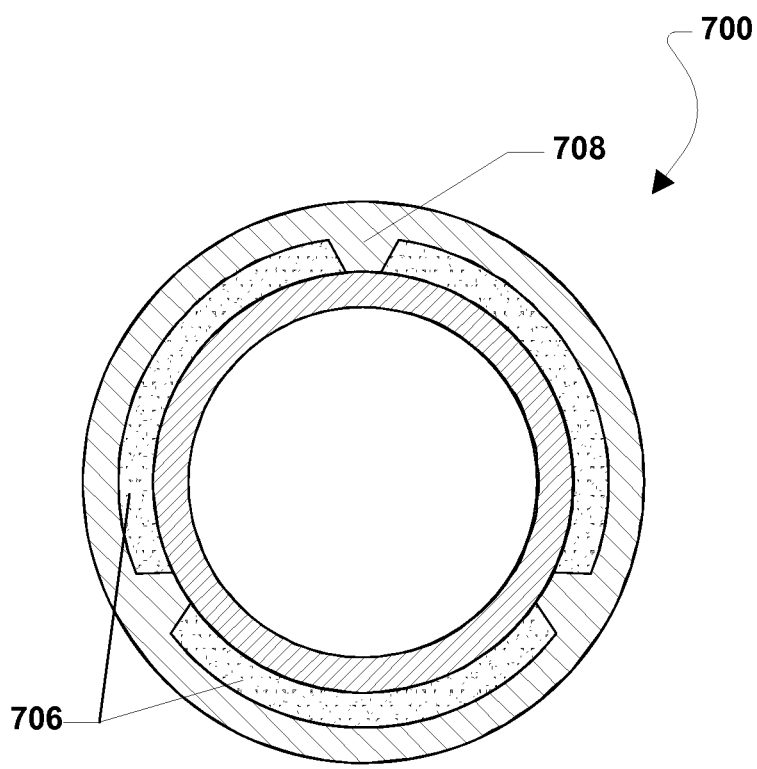
FIG. 7 is a cross-section view of a third embodiment of a sheath for a vascular implant delivery device.

As shown in FIG. 5, twelve longitudinal voids 506 and twelve implant support structures 508 can be formed sheath 500. Alternatively, some other number of longitudinal voids can be formed in the inner surface. For example, FIG. 6 shows a second embodiment of a sheath 600 that is formed with six longitudinal voids 606 and six implant support structures 608. Further, FIG. 7 shows a third embodiment of a sheath 700 that is formed with three longitudinal voids 706 and three implant support structures 708. In a particular embodiment, depending on the number of longitudinal voids and implant support structures, the sheath can contact a portion of the outer surface 512 of the vascular implant 510.

In a particular embodiment, the sheath 500 does not contact more than fifty percent (50%) of the outer surface 512 of the vascular implant 510. In another embodiment, the sheath 500 does not contact more than thirty-five percent (35%) of the outer surface 512 of the vascular implant 510. In another embodiment, the sheath 500 does not contact more than thirty percent (30%) of the outer surface 512 of the vascular implant 510. In yet another embodiment, the sheath 500 does not contact more than twenty-five percent (25%) of the outer surface 512 of the vascular implant 510. In still another embodiment, the sheath 500 does not contact more than twenty percent (20%) of the outer surface 512 of the vascular implant 510. In still yet another embodiment, the sheath 500 does not contact more than fifteen percent (15%) of the outer surface 512 of the vascular implant 510. In another embodiment, the sheath 500 does not contact more than ten percent (10%) of the outer surface 512 of the vascular implant 510. In another embodiment, the sheath 500 contacts at least five percent (5%) of the outer surface 512 of the vascular implant 510.

Figure 8:
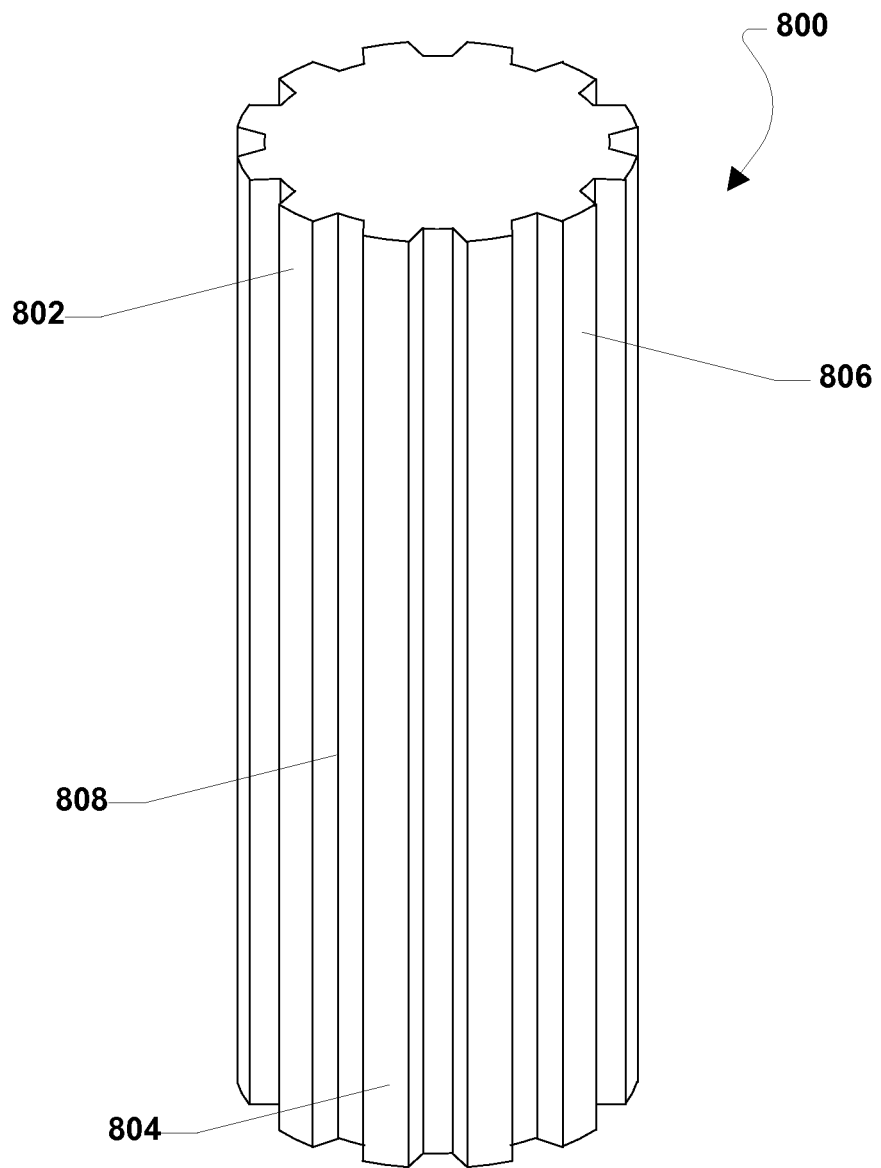
FIG. 8 is a perspective view of a first embodiment of a mandrel for forming a sheath.

It can be appreciated that each of the embodiments described in conjunction with FIG. 5 through FIG. 7 can be formed using an extrusion process. Alternatively, these embodiments can be formed on a mandrel. FIG. 8 depicts an example of a mandrel, generally designated 800, on which a sheath can be formed, e.g., the sheath depicted in FIG. 5.

As shown, the mandrel 800 can include a proximal end 802 and a distal end 804. The mandrel 800 can also include an outer periphery 806. The outer periphery 806 of the mandrel 800 can be formed with a plurality of longitudinal voids 808 radially spaced there around. In a particular embodiment, material can be formed around the mandrel 800 and cured. The interior of a sheath formed on the mandrel can take the form of the mandrel.

Figure 9:
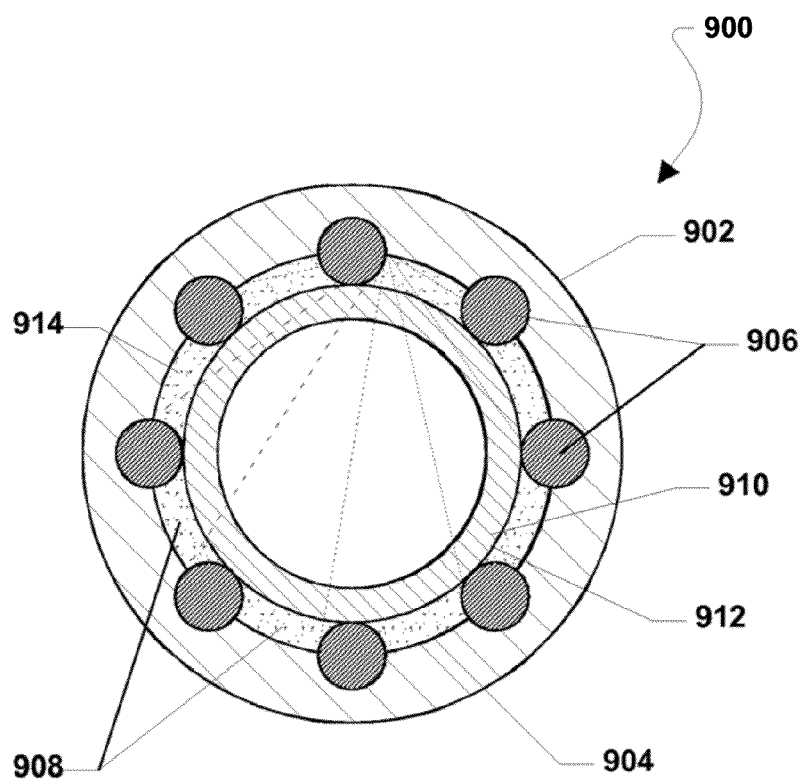
FIG. 9 is a cross-section view of a fourth embodiment of a sheath for a vascular implant delivery device.

Referring now to FIG. 9, a fourth embodiment of a sheath is shown and is generally designated 900. The sheath 900 is shown in cross-section. Further, the sheath 900 can be used as an outer sheath in conjunction with a vascular implant delivery device, e.g., the vascular implant delivery device 100 shown in FIG. 1 through FIG. 4.

As illustrated, the sheath 900 can include an outer surface 902 and an inner surface 904. The sheath 900 can also include a lumen that is bound by the inner surface 904. The sheath 900 can include a plurality of longitudinal fibers 906 that can extend longitudinally along a length of the sheath 900. The fibers 906 can be shaped as shown. However, the fibers 906 can be shaped otherwise, e.g., rectangular, triangular, irregular, etc. Further, the fibers 906 can be lubricious or coated with a lubricious coating. Additionally, the fibers 906 can extend in a non-linear fashion along the length of the sheath 900. For example, the fibers 906 can be extend helically along the length of the sheath 900 and the fibers 906 can cross each other at various locations along the length of the sheath 900.

Each longitudinal fiber 906 can extend radially from the inner surface 904 into the lumen of the sheath 900 so that only a portion of each longitudinal fiber 906 is embedded within the sheath 900. For example, at least fifty percent (50%) of each longitudinal fiber is embedded within the sheath 900. In another embodiment, at least fifty-five percent (55%) of each longitudinal fiber is embedded within the sheath 900. In yet another embodiment, at least sixty percent (60%) of each longitudinal fiber is embedded within the sheath 900. In still another embodiment, at least sixty-five percent (65%) of each longitudinal fiber is embedded within the sheath 900. In another embodiment, at least seventy percent (70%) of each longitudinal fiber is embedded within the sheath 900. In yet another embodiment, not more than eighty-five percent (85%) of each longitudinal fiber is embedded within the sheath 900.

As shown in FIG. 9, a plurality of longitudinal voids 908 can be formed in the sheath 900. Specifically, each longitudinal void 908 can be formed between adjacent longitudinal fibers 906, i.e., between the portions of the longitudinal fibers 906 that extend from the inner surface 904 of the sheath 900.

In a particular embodiment, the longitudinal voids 908 can be equally spaced around the inner surface 904 of the sheath 900.

In a particular embodiment, a vascular implant 910 can be slidably disposed within the sheath 900. The vascular implant 910 can be a stent, a stent graft, an intravenous filter, or some other implant that is delivered to a patient using a cannulated delivery device. Alternatively, the vascular implant 910 can be an angioplasty balloon that is temporarily deployed and inflated to treat a patient. FIG. 9 indicates that the vascular implant 910 can include an outer surface 912.

As shown in FIG. 9, the longitudinal fibers 906 can act as implant support structures and the longitudinal fibers 906 can contact the outer surface 912 of the vascular implant 910. Moreover, each longitudinal void 908 can allow a lubricant 914 to be introduced into the sheath 900 around the vascular implant 910. In a particular embodiment, the lubricant can be saline solution.

FIG. 9 indicates that each longitudinal void 908 can be at least partially filled with the lubricant and the lubricant can surround the vascular implant 910. The lubricant can reduce friction between the longitudinal fibers 906 and the vascular implant 910. As such, the force require to expel the vascular implant 910 from the sheath is substantially reduced.

As shown in FIG. 9, the sheath 900 can include eight longitudinal fibers 906 and eight longitudinal voids 908. Alternatively, the sheath 900 can include some other number of longitudinal fibers 906 and longitudinal voids 908. For example, FIG. 10 shows a fifth embodiment of a sheath 1000 that includes four longitudinal fibers 1006 and four longitudinal voids 1008.

In a particular embodiment, the sheath 900, e.g., the longitudinal fibers 908 of the sheath 900, can contact a portion of the outer surface 912 of the vascular implant 910. The contact between the sheath 900 and the vascular implant 910 can depend on the number of longitudinal fibers 906 within the sheath 900.

In a particular embodiment, the sheath 900 does not contact more than fifty percent (50%) of the outer surface 912 of the vascular implant 910. In another embodiment, the sheath 900 does not contact more than thirty-five percent (35%) of the outer surface 912 of the vascular implant 910. In another embodiment, the sheath 900 does not contact more than thirty percent (30%) of the outer surface 912 of the vascular implant 910. In yet another embodiment, the sheath 900 does not contact more than twenty-five percent (25%) of the outer surface 912 of the vascular implant 910. In still another embodiment, the sheath 900 does not contact more than twenty percent (20%) of the outer surface 912 of the vascular implant 910. In still yet another embodiment, the sheath 900 does not contact more than fifteen percent (15%) of the outer surface 912 of the vascular implant 910. In another embodiment, the sheath 900 does not contact more than ten percent (10%) of the outer surface 912 of the vascular implant 910. In another embodiment, the sheath 900 contacts at least five percent (5%) of the outer surface 912 of the vascular implant 910.

Figure 10:
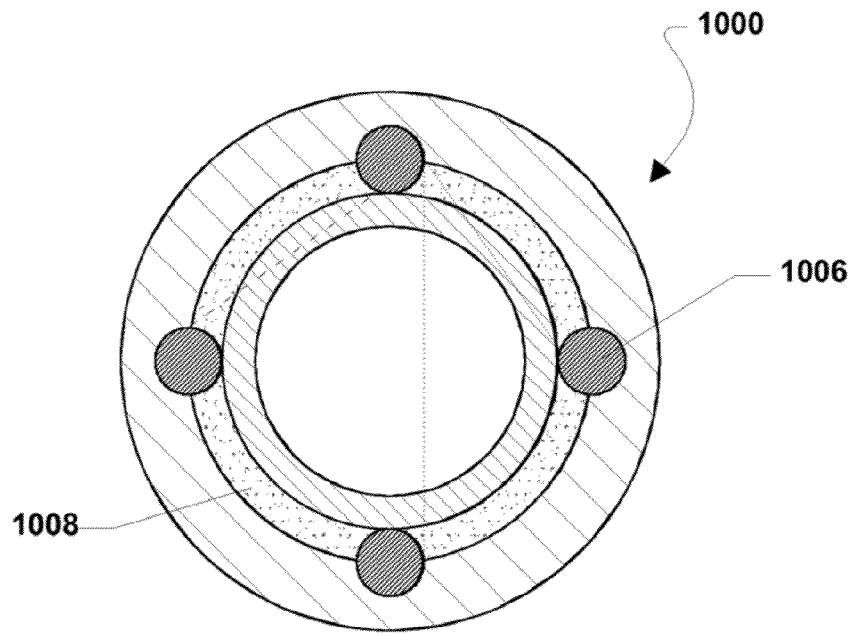
FIG. 10 is a cross-section view of a fifth embodiment of a sheath for a vascular implant delivery device.
Figure 11:
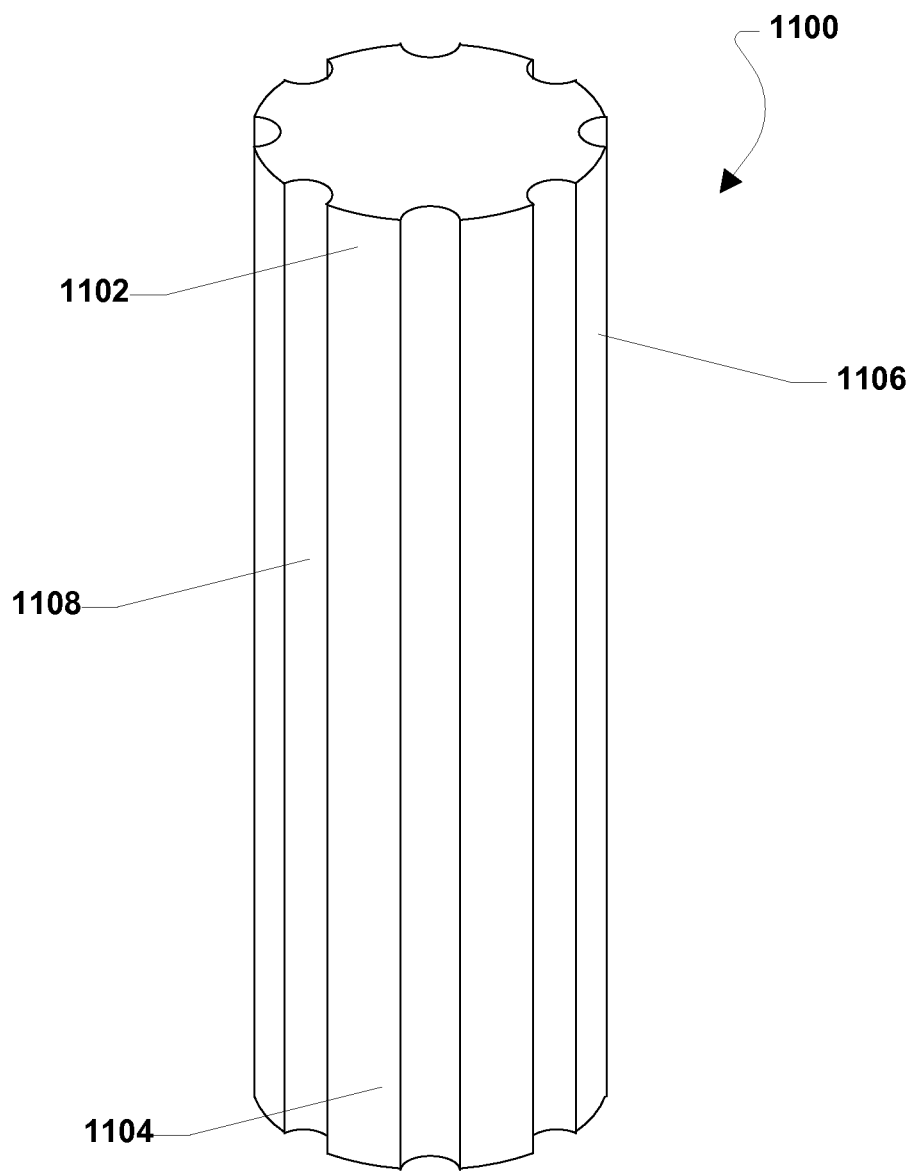
FIG. 11 is a perspective view of a second embodiment of a mandrel for forming a sheath.

It can be appreciated that each of the embodiments described in conjunction with FIG. 9 and FIG. 10 can be formed using an extrusion process. The longitudinal fibers can be longitudinally added to the extruded material as it is extruded. In an alternative embodiment, these embodiments can be formed on a mandrel. FIG. 11 depicts an example of a mandrel, generally designated 1100, on which a sheath can be formed, e.g., the sheath depicted in FIG. 9.

As shown, the mandrel 1100 can include a proximal end 1102 and a distal end 1104. The mandrel 1100 can also include an outer periphery 1106. The outer periphery 1106 of the mandrel 1100 can be formed with a plurality of longitudinal voids 1108 radially spaced there around. In a particular embodiment, a longitudinal fiber can be placed in each longitudinal void 1108. Thereafter, a polymeric material can be formed around the mandrel 1100 and cured. The longitudinal fibers can be embedded into the material, as described above.

Description of a Method of Installing a Vascular Implant

Figure 12:
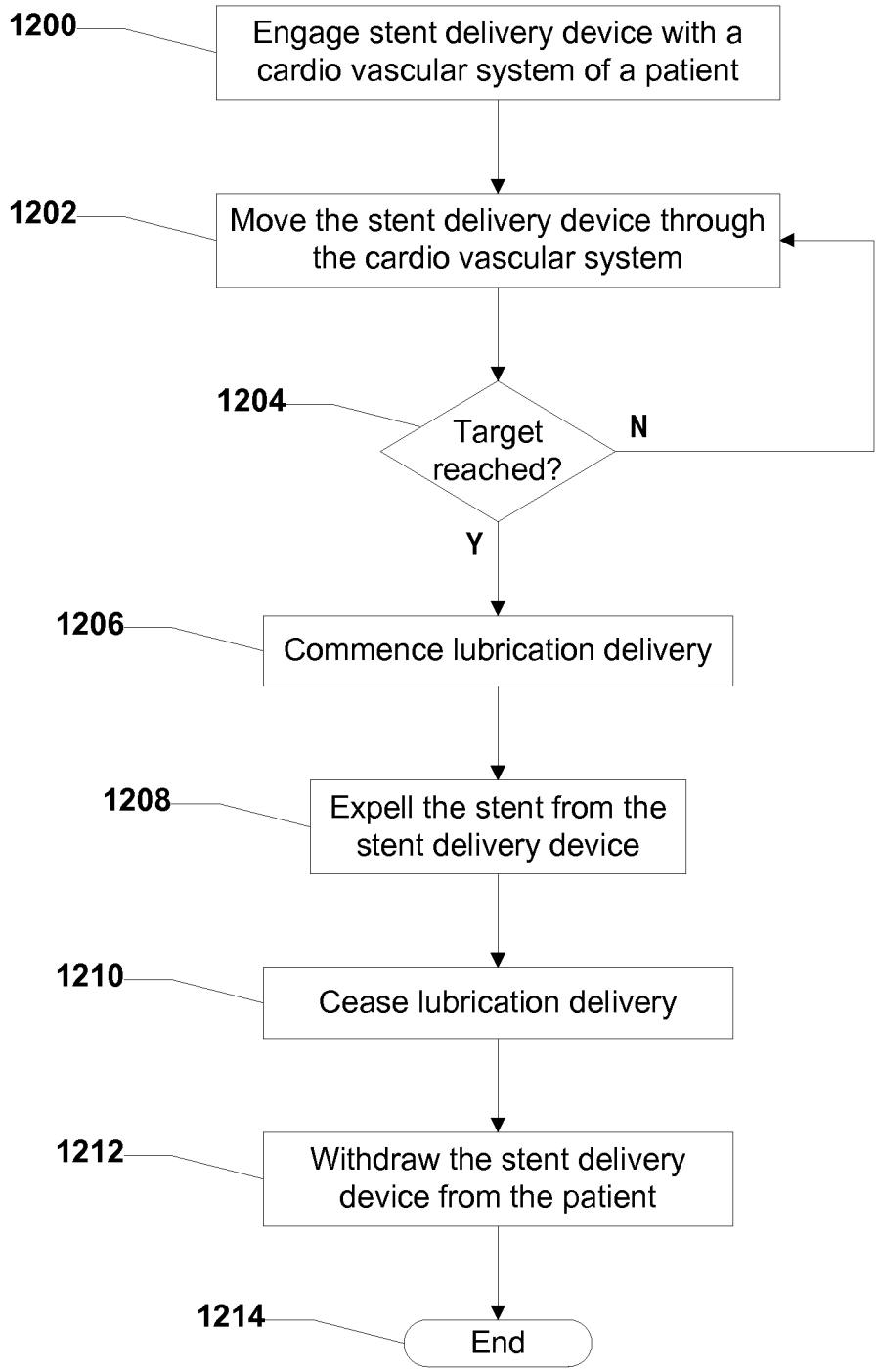
FIG. 12 is a flow chart illustrating one method of installing and deploying a vascular implant.

Referring now to FIG. 12, a method of installing a vascular implant is shown and commences at block 1200. At block 1200, a vascular implant delivery device can be engaged with a cardio vascular system of a patient. At block 1202, the delivery device can be moved through the cardio vascular system of the patient.

Moving to decision step 1204, it can be determined whether a target within the cardio vascular system is reached. The location of the vascular implant within the patient can be determined using fluoroscopy and one or more radiopaque bands on the vascular implant, the vascular implant delivery device, or both. If the target is not reached, the method can return to block 1202 and the delivery device can be moved within the cardio vascular system. Then, the method can continue as described herein.

Returning to decision step 1204, if the target is reached, the method can proceed to block 1206 and lubrication delivery can be commenced. At block 1208, a vascular implant can be expelled from the delivery device. Further, at block 1210, lubrication delivery can be ceased. At block 1212, the delivery device can be withdrawn from the patient. Then, the method ends at state 1214. In an alternative embodiment, a lubrication delivery can commence after step 1202, e.g., if the implant is in contact with an inner diameter of the sheath while being advanced throughout the entire length of the sheath.

As described herein, the method can be used to install a vascular implant within a patient. The vascular implant can be a stent, a stent graft, an intravenous filter, or some other implant that is delivered to a patient using a cannulated delivery device. Alternatively, the vascular implant can be an angioplasty balloon that is temporarily deployed and inflated to treat a patient.

Description of Vascular Implants

FIG. 13 through FIG. 19 illustrate examples of implants that can be delivered using the device described herein. FIG. 13 and FIG. 14 depict a stent 1300. The stent 1300 can be moved through a delivery device in a collapsed configuration, shown in FIG. 13. After the stent 1300 is deployed, it can move to an expanded configuration, shown in FIG. 14.

Figures 15, 16:
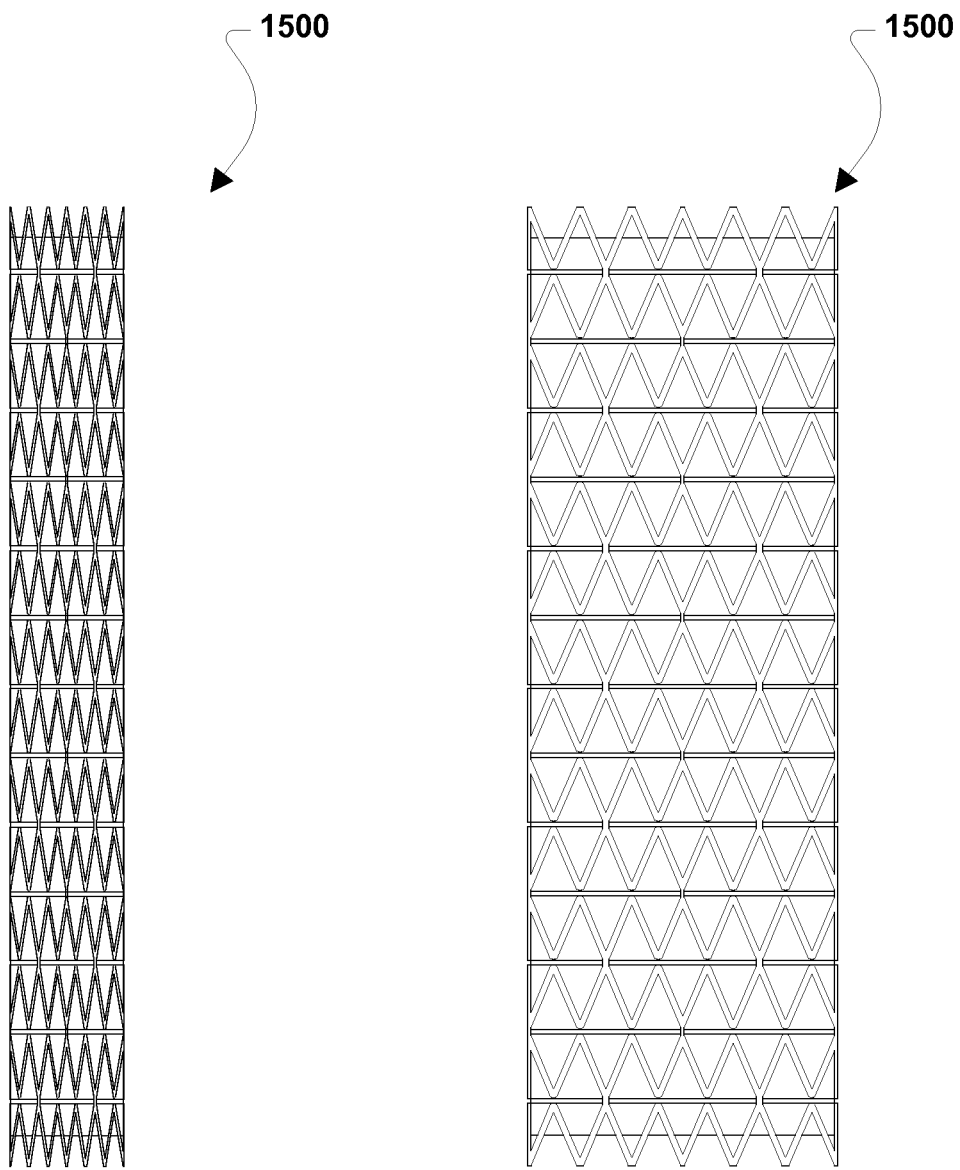
FIG. 15 is a plan view of a stent graft in a collapsed configuration.
FIG. 16 is a plan view of the stent graft in an expanded configuration.

FIG. 15 and FIG. 16 depict a stent graft 1500. The stent 1500 can be moved through a delivery device in a collapsed configuration, shown in FIG. 15. After the stent graft 1500 is deployed, it can move to an expanded configuration, shown in FIG. 16.

Further, FIG. 17 and FIG. 18 depict an intravenous filter 1700. The filter 1700 can be moved through a delivery device in a collapsed configuration, shown in FIG. 17. After the filter 1700 is deployed, it can move to an expanded configuration, shown in FIG. 18.

Figure 19:
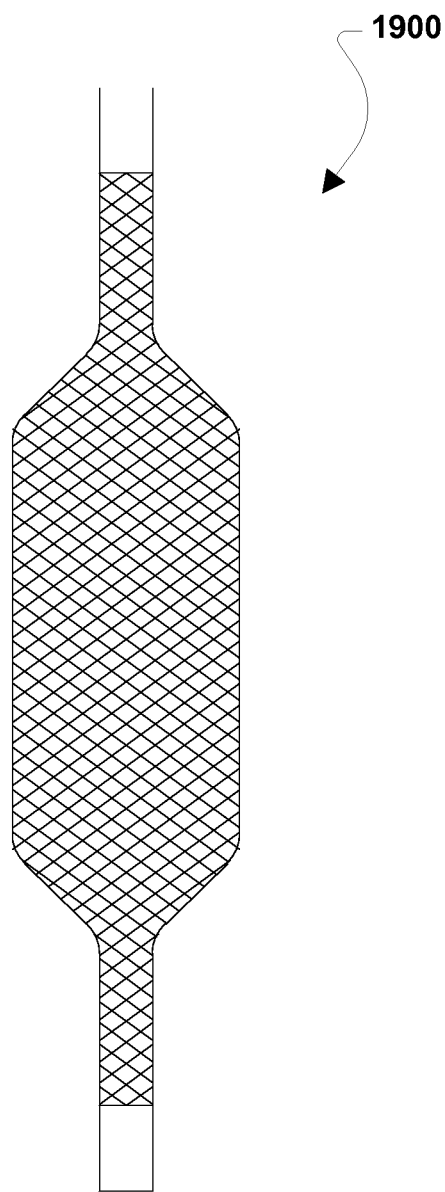
FIG. 19 is a plan view of an angioplasty balloon in an expanded configuration.

FIG. 19 illustrates an angioplasty balloon 1900. The angioplasty balloon 1900 can be moved through a delivery device in a collapsed configuration, not shown. Moreover, the angioplasty balloon 1900 can be deployed and expanded, as shown in FIG. 19. After treatment, the angioplasty balloon 1900 can be returned to the collapsed configuration and retracted back into the delivery device.

CONCLUSION

With the configuration of embodiments described above, embodiments described herein provide one or more sheaths that can be configured to minimize friction between the sheath and an implant to be moved there through. As such, the size of the sheath can be minimized, e.g., less than 5 French size, to minimize discomfort to a patient in which the sheath is installed. Further, as the size of the sheath is reduced, the configuration of an embodiment described herein can also minimize the force required to expel an implant from the sheath. Moreover, embodiments described herein can allow a lubricant to be delivered through the sheath around the implant to further minimize friction and the delivery force.

Additionally, embodiments herein can be internally coated with a film or coating having a relatively low coefficient of friction, e.g., less than 0.15. Examples of such coatings can include diamond film and tungsten disulfide powder.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A vascular implant delivery system, comprising:
   a vascular implant;
   a body;
   a syringe attachment port formed in the body;
   an outer sheath extending from the body, wherein the outer sheath comprises a distal end configured to receive the vascular implant, the outer sheath having a lumen that extends from the distal end to a proximal end of the outer sheath, the lumen capable of fluid communication with the syringe attachment port;
   at least three implant support structures extending radially inward from the distal end of the outer sheath, wherein the implant support structures are partially embedded in the lumen of the outer sheath and include a lubricious coating and are in direct contact with an outer surface of the vascular implant to support and guide the vascular implant;
   voids formed between adjacent implant support structures, the voids configured for receiving a lubricant; and
   an inner carrier catheter slidably disposed within the outer sheath.

2. The system of claim 1, wherein the outer sheath defines an inner surface of the lumen and wherein the voids comprise at least three longitudinal voids formed in the inner surface of the outer sheath.

3. The system of claim 2, wherein each implant support structure is formed between adjacent longitudinal voids.

4. The system of claim 1, wherein each implant support structure comprises a longitudinal fiber partially embedded within the outer sheath and wherein each void is formed between adjacent longitudinal fibers.

5. The system of claim 4, wherein each longitudinal fiber extends along a length of the outer sheath.

6. The system of claim 2, wherein each longitudinal void is configured to deliver the lubricant around the vascular implant as the vascular implant is moved through the outer sheath.

7. The system of claim 1, wherein the implant support structures do not contact more than fifty percent (50%) of the outer surface of the vascular implant.

8. The system of claim 7, wherein the implant support structures do not contact more than thirty-five percent (35%) of the outer surface of the vascular implant.

9. The system of claim 8, wherein the implant support structures do not contact more than thirty percent (30%) of the outer surface of the vascular implant.

10. The system of claim 9, wherein the implant support structures do not contact more than twenty-five percent (25%) of the outer surface of the vascular implant.

11. The system of claim 10, wherein the implant support structures do not contact more than twenty percent (20%) of the outer surface of the vascular implant.

12. The system of claim 11, wherein the implant support structures do not contact more than fifteen percent (15%) of the outer surface of the vascular implant.

13. The system of claim 12, wherein the implant support structures do not contact more than ten percent (10%) of the outer surface of the vascular implant.

14. The system of claim 13, wherein the implant support structures contact at least five percent (5%) of the outer surface of the vascular implant.

15. The system of claim 1, wherein the implant support structures support and guide the vascular implant as it moves along the implant support structures through the outer sheath.

16. The system of claim 1, wherein the outer sheath defines an inner surface and wherein the implant support structures are formed in the inner surface of the outer sheath from the material of the inner surface of the outer sheath.

17. The system of claim 1, wherein at least one of the at least three implant support structures has a generally trapezoidal-shaped cross section.

18. A vascular implant delivery device, comprising:
    a vascular implant;
    a syringe attachment port;
    an outer sheath having an outer surface, an inner surface, and a lumen bound by the inner surface, the lumen extending from a distal end to a proximal end of the outer sheath and being capable of fluid communication with the syringe attachment port;
    at least three longitudinal fibers partially embedded within the outer sheath, wherein each longitudinal fiber at least partially extends radially into the lumen of the outer sheath, and wherein the longitudinal fibers are lubricious and are configured to be in direct contact with an outer surface of the vascular implant loaded within the outer sheath to support and guide the vascular implant; and
    voids formed between adjacent longitudinal fibers, the voids configured for receiving a lubricant.

19. The device of claim 18, wherein each longitudinal fiber extends along a length of the outer sheath.

20. The device of claim 18, wherein the longitudinal fibers support and guide the vascular implant as it moves along the longitudinal fibers through the outer sheath.

21. An implant delivery assembly, comprising:
    a body;
    a syringe attachment port formed in the body;
    an outer sheath extending from the body, wherein the outer sheath comprises a lumen extending from a distal end to a proximal end of the outer sheath, the lumen configured to fluidly communicate with the syringe attachment port, the outer sheath including at least three implant support structures extending radially inward from the distal end of the outer sheath, wherein the implant support structures are partially embedded in the lumen of the outer sheath and include a lubricious coating, and wherein voids are formed between adjacent implant support structures, the voids configured to receive a lubricant;

an inner carrier catheter slidably disposed within the outer sheath; and a vascular implant slidably disposed within the distal end of the outer sheath, wherein the implant support structures are in direct contact with an outer surface of the vascular implant.

22. The assembly of claim 21, wherein the vascular implant comprises a stent, a stent graft, an intravenous filter, an angioplasty balloon, or a combination thereof.

23. The assembly of claim 22, wherein the implant support structures comprise at least three longitudinal fibers partially embedded within the outer sheath, and wherein each longitudinal fiber at least partially extends radially into the lumen of the outer sheath.

24. The assembly of claim 21, wherein the implant support structures support and guide the vascular implant as it moves along the implant support structures through the outer sheath.

* * * * *